United States Patent [19]
Green

[11] Patent Number: 5,125,118
[45] Date of Patent: Jun. 30, 1992

[54] FEMALE URINE SPECIMEN COLLECTION DEVICE

[76] Inventor: Edwin J. Green, 1018 Westminister Dr., Greensboro, N.C. 27410

[21] Appl. No.: 695,991

[22] Filed: May 6, 1991

[51] Int. Cl.$^5$ ............................................. A47K 11/12
[52] U.S. Cl. ...................................... 4/144.2; 4/144.4; 128/761; 604/329
[58] Field of Search .............................. 4/144.1–144.4; 128/761; 604/329

[56] References Cited

U.S. PATENT DOCUMENTS

| | | | |
|---|---|---|---|
| 1,510,973 | 10/1924 | Behan | 604/329 |
| 3,432,866 | 3/1969 | Schwartz | 4/144.3 X |
| 3,556,102 | 1/1971 | Davis | 3/144.3 X |
| 3,680,543 | 8/1972 | Cox | 604/329 X |
| 4,496,355 | 1/1985 | Hall et al. | 4/144.3 X |
| 4,559,649 | 12/1985 | Barnett | 4/144.4 X |

*Primary Examiner*—Charles E. Phillips

[57] ABSTRACT

A urine specimen collection device is presented for providing contaminant-free samples from female donors. The device includes an upper conduit which is placed within the interior genital region of a female patient. The specimen provided is delivered through the conduit into a releasable collection container attached therebelow. As a result of the interior placement of the conduit within the female, a contaminant-free sample is obtained for greater urinalysis accuracy.

5 Claims, 1 Drawing Sheet

FEMALE URINE SPECIMEN COLLECTION DEVICE

BACKGROUND OF THE INVENTION

1. Field Of The Invention

This invention relates to a disposable device for use in taking urine samples from females. More specifically, the invention relates to a two section collection assembly whereby the upper section is placed against the female genitalia and provides a conduit for a releasable bottom section consisting of a collection container or cup. The upper section is easily positioned with respect to the urethral orifice to directly obtain a urine specimen which is unadulterated.

2. Description Of The Prior Art And Objectives Of The Invention

Urinalysis is an essential factor of any medical examination and most women have a difficult time in providing a representative urine specimen with conventional specimen apparatus due to the anatomical proximity of the urethra and the labia majora and labia minora which surround the vaginal orifice. Even with detailed instructions from medical personnel, obtaining a urine sample free from extraurethral contamination has been difficult utilizing conventional apparatus which is either inserted into or which fits outwardly of the female pelvic area. Some specimen collection devices in the past have been somewhat effective for certain patients while other devices have caused the specimen donor to feel annoyance and be inconvenienced due to the actual or anticipated prospect of urinating on her hands, clothing or along the outside of the collection device during specimen delivery. Specific prior art devices have been configured to fit partially into the vaginal opening. Devices of this nature often are difficult to use by certain donors in that the devices are not configured for their particular body sizes and spacings. Other urine collection devices which are relatively easy to use by the donors are positioned externally of the genitalia, but allow for extraurethral contamination.

Therefore, it is one objective of the present invention to provide a urine specimen collection device for use by females which will provide a relatively contaminant free urine specimen for greater urinalysis accuracy.

It is still another objective of the present invention to provide a urine specimen collection device which consists of a tubular upper section which has a flattened frusto-conical shape for insertion into the female genitalia against the labia minora to obtain a contaminant free urine sample.

It is still another objective of the present invention to provide a urine specimen collection device which includes a collection cup which is releasably affixed to the upper frusto-conical section.

It is still another objective of the present invention to provide a female urine specimen collection device which may be made of biodegradable paper components for environmentally safe disposal.

It is still another objective of the present invention to provide a female urine specimen collection device which allows for each section to be stacked or nestled in quantities for economy in transportation and storage.

Various other advantages and benefits of the present invention become apparent to those skilled in the art as a more detailed description is presented below.

SUMMARY OF THE INVENTION

The aforesaid and other objectives are realized by providing a specimen collection device which can be easily and conveniently used by females to provide a contaminant-free urine sample. The device consists of an upper conduit which is positionable within the female genitalia. The upper section consists of a tubular frusto-conical portion which has an elliptical opening at the top. A round, smooth lip surrounds the opening and at the lower end of the frusto-conical portion is a circular base having a dependent flange. A means to attach the conduit to a conventional urine collection cup is provided whereupon the specimen donor can easily utilize the collection device. Thereafter the collection cup is removed from the conduit whereupon the filled collection cup can be taken to a laboratory and urinalysis completed. The tubular conduit and collection cup can be both made from biodegradable paper products and the upper section can be easily separated from the lower section and can be stored separate from the lower section in compact, stacked fashion.

DESCRIPTION OF THE PREFERRED EMBODIMENT

Figure 1:
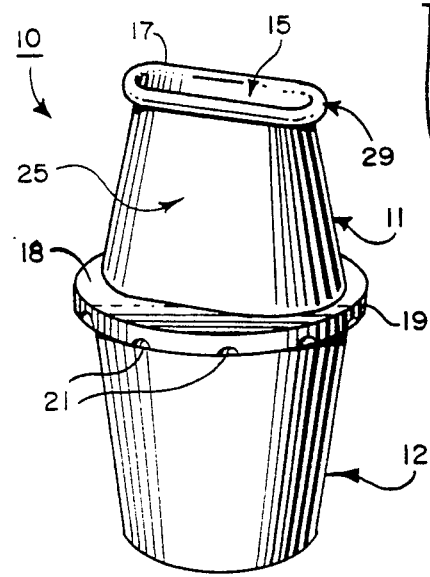
FIG. 1 demonstrates the female urine collection device of the invention with the conduit section released from the collection container in a perspective side view.
Figure 4:
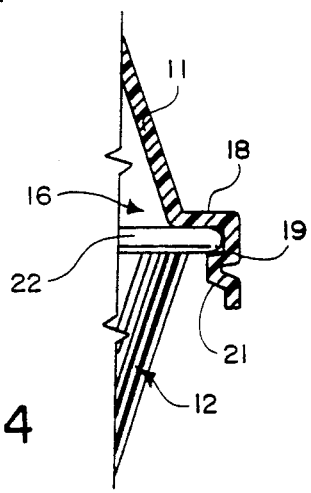
FIG. 4 depicts an enlarged partial view of the conduit base flange and collection container lip in engagement.
Figure 2:
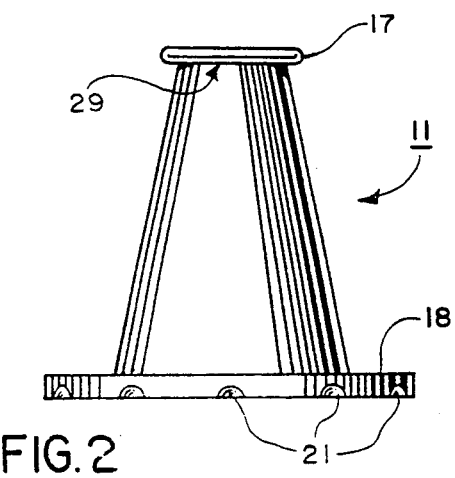
FIG. 2 illustrates a front elevational view of the tubular frusto-conical conduit section.
Figure 3:
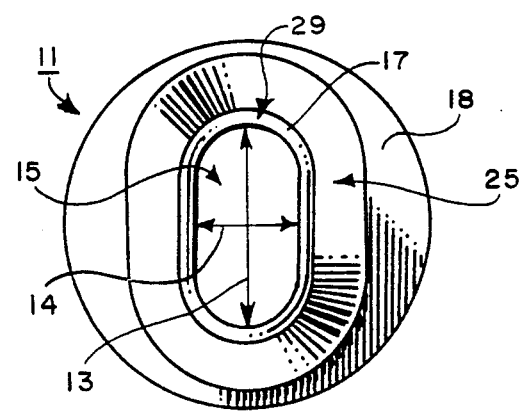
FIG. 3 shows a top plan view of the conduit section.

The preferred form of the invention is shown in FIGS. 1, 2 and 3. As seen in FIG. 1, the upper section of the specimen collection device comprises a somewhat flattened frusto-conical conduit portion having an elliptical opening at the top which is surrounded by a smooth, rounded lip. The base of the conduit as shown in FIGS. 3 and 6 is circular and open whereby fluids entering the upper opening will pass below into the collection container, as understood from FIGS. 1 and 5. The collection container and conduit releasably attach to each other for ease and convenience in handling. In FIGS. 2 and 4 a series of projections are positioned on the inside wall of the depending base lip. The lip is flexible whereby the collection container will easily slide against and "lock" in place against the bottom surface of the conduit base.

Figure 5:
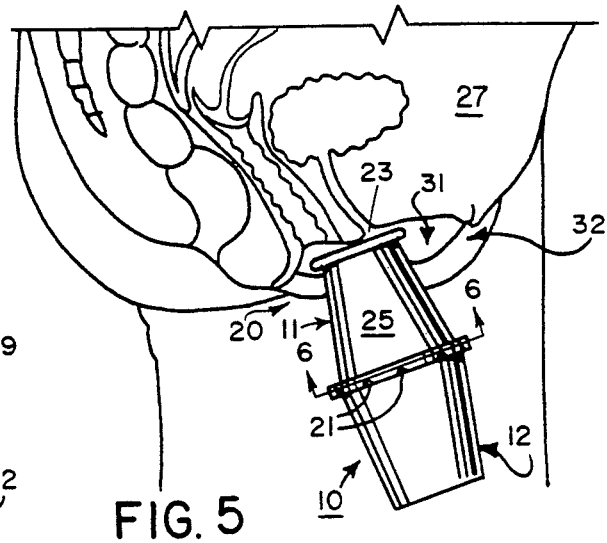
FIG. 5 pictures in schematic fashion the specimen collection device of the invention as placed within the female genitalia.
Figure 6:
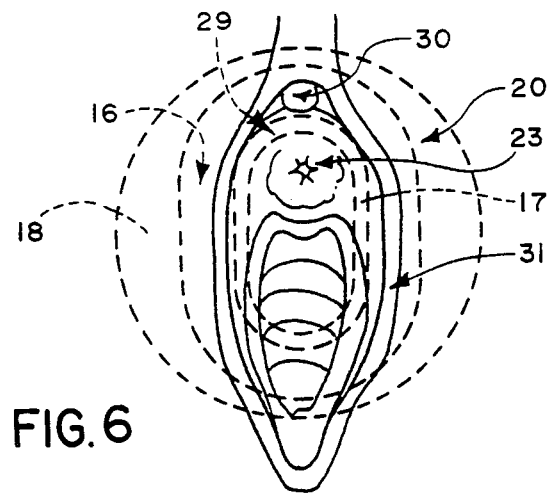
FIG. 6 represents a view along lines 6-6 of FIG. 5 with the collection cup removed.

In use the specimen collection device is assembled and inserted with the elliptical opening of the conduit placed within the female genitalia inside the labia minora to a forward position against the clitoris and substantially over the urethral orifice as shown in FIGS. 5 and 6. So placed, the donor can provide a substantially contaminant-free urine specimen whereby the urine will not contact the clitoris, labia minora or labia majora and collect contaminants prior to entry through the elliptical opening. Fluids entering the conduit pass directly into the collection container below. The donor can thereafter remove the specimen collection device, and present it to medical personnel for analysis. The conduit portion is removed from the collection container and analysis begun. Both the conduit and collection container are formed from a relatively inexpensive biodegradable paper or plastic for ease and safety in disposal.

DETAILED DESCRIPTION OF THE DRAWINGS AND OPERATION OF THE INVENTION

For a more complete understanding of the invention and its operation, turning now to the drawings, FIG. 1 demonstrates female urine specimen collection device 10 comprising in combination an upper tubular, somewhat flattened frusto-conical conduit section 11 which is releasably engagable with lower collection section 12. Collection device 10 may be formed from paper, plastic or other materials and preferably is biodegradable to prevent future solid waste disposal problems. Collection container 12 is conventional and will hold four to six (4-6) ounces of liquid specimen although other sizes and shapes may be employed as required. Upper tubular conduit section 11 and lower container section 12 can be easily stored and transported in stacked fashion in convenient quantities and can be quickly assembled for use by inexperienced female patients or other specimen donors. The tubular conduit 11 has a flattened frusto-conical configuration as is shown in a front elevational view in FIG. 2 which clearly illustrates the narrow width of section 11 as compared to the length of as seen in FIG. 1. As further illustrated in the top plan view of conduit 11 in FIG. 3, the longitudinal axis 13 of elliptical opening 15 is seen at the top of frusto-conical conduit 11. As further shown in FIG. 3, lateral axis 14 is approximately one-half (½) the length of longitudinal axis 13 to provide a convenient shape for ease in insertion into the female genitalia during use. Rim 17 which is rounded and smooth encircles elliptical opening 15 to assist in insertion into the female genitalia region 20 shown in FIG. 5.

Conduit section 11 and collection section 12 are releasably engaged as shown in FIG. 4 whereby base 18 includes a flange 19 which depends therefrom. Flange 19 includes a means which consists of an inwardly formed blunted projection 21 positioned on the inside wall of flange 19 for grasping collection container lip 22. As shown in FIGS. 1 and 5, a plurality of projections 21 are formed in container lip 22 and as would be further understood, projections 21, due to the integral formation in flange 19 will allowing convenient release and attachment by providing flexibility to flange 19.

Specimen collection device 10 can be used by inexperienced female patients or donors by manual insertion into the genital region 20 where conduit rim 17 will come to rest below urethral orifice 23 as seen in FIGS. 5 and 6. As further shown in FIG. 5, flattened side 25 is so positioned so longitudinal axis 13 runs from the front to the back of donor 27 whereas lateral axis 14 of elliptical opening 15 runs from side to side. In the use position, front edge 29 of conduit rim 17 is positioned forwardly, against clitoris 30 (FIGS. 5 and 6) whereupon opening 15 is directly below urethral orifice 23 as illustrated in FIG. 6. Rim 17 is inside labia minora 31 and labia majora 32 as also pictured in FIG. 6, thus assuring a contaminant-free sample since urine will not contact either labia before entry into collection device 10 through opening 15. Once the specimen has been delivered into conduit 11 it passes therethrough, beyond base opening 16 and into collection container 12 below. After delivery, the donor can easily remove urine collection device 10 from her genitalia region 20 where the specimen can be presented to lab personnel for urinalysis.

The illustrations and examples provided herein are for explanatory purposes and other shapes and sizes of the collection device can be utilized and the drawings presented are not intended to limit the scope of the appended claims.

I claim:

1. A urine specimen conduit for a female comprising: a flattened frusto-conical portion, said frusto-conical portion defining a horizontal substantially elliptically-shaped opening at the upper end, a rim, said rim attached to the top of said frusto-conical portion surrounding said opening and being of a size as to fit inside the users labia minora and surround the users urethral orifice, a circular horizontal base, said base joined to the bottom of said frusto-conical portion, said flattened frusto-conical portion tapering downwardly and outwardly from said rim to define an opening around which said base is attached, said elliptical opening being in generally parallel alignment with said base, a depending flange having an inside surface and an outside surface, said flange positioned around the periphery of said base, means to attach said base to a specimen container, said attaching means comprising a plurality of projections, positioned along said inside of said flange, and said flange being flexible to allow releasable engagement between said projections and said specimen container.

2. A female urine collection device comprising in combination: a conduit section and a specimen container section, said conduit comprising: a tubular portion, said tubular portion defining a linear horizontal opening in the form of a substantially elliptical shape at the top thereof, a rim attached to the top of said tubular portion around said opening and being of a size as to fit inside the users labia minora and surround the users urethral orifice, a horizontally aligned base in generally parallel alignment with said linear opening, said tubular portion comprising a flattened frusto-conical configuration which tapers downwardly and outwardly from said rim to define a bottom opening around which said base is attached, a depending flange having an inside surface and an outside surface, said flange positioned around the periphery of said base, means to attach said base to a specimen container, said attaching means comprising a plurality of projections, positioned along said inside of said flange, and said flange being flexible to allow releasable engagement between said projections and said specimen container.

3. The collection device of claim 2 wherein said specimen collection section comprises a disposable cup.

4. The collection device of claim 2 wherein said conduit and collection cup are formed from plastic.

5. The collection device of claim 2 wherein said conduit and collection cup are formed from biodegradable paper.

* * * * *